United States Patent [19]

Swanbeck

[11] 4,234,603
[45] Nov. 18, 1980

[54] SKIN-TREATING COMPOSITION AND VEHICLE FOR SKIN-TREATING AGENTS

[75] Inventor: Gunnar P. E. Swanbeck, Vaxholm, Sweden

[73] Assignee: Medisan AB, Upsala, Sweden

[21] Appl. No.: 882,810

[22] Filed: Feb. 28, 1978

Related U.S. Application Data

[63] Continuation of Ser. No. 712,066, Aug. 5, 1976, which is a continuation of Ser. No. 571,746, Apr. 25, 1975, abandoned, which is a continuation of Ser. No. 322,197, Jan. 9, 1973, abandoned.

[30] Foreign Application Priority Data

Jan. 10, 1972 [GB] United Kingdom ................ 1073/72

[51] Int. Cl.² .................... A61K 7/48; A61K 47/00
[52] U.S. Cl. .................................. 424/365; 424/168;
424/359
[58] Field of Search ............................. 424/358, 365

[56] References Cited

U.S. PATENT DOCUMENTS

| | | | |
|---|---|---|---|
| 2,322,565 | 6/1943 | Cole | 424/322 X |
| 2,460,776 | 2/1949 | Vincent | 424/322 X |
| 3,660,296 | 5/1972 | Lavial | 424/322 |
| 3,705,239 | 12/1972 | Gregory | 424/322 X |

FOREIGN PATENT DOCUMENTS 98238 11/1959 Czechoslovakia ....................... 424/365

OTHER PUBLICATIONS

Chem. Abs., 1962, vol. 56, pp. (13030).

*Primary Examiner*—Dale R. Ore
*Attorney, Agent, or Firm*—Haseltine, Lake & Waters

[57] ABSTRACT

The present invention relates to a skin-treating composition comprising an aqueous phase in which urea and a salt are dissolved. The said aqueous phase should have a pH value of 2–8, especially 3–7. Optionally, the composition of the invention may comprise a lipid phase, wetting or emulsifying agents and amino acids. The composition is per se beneficial for the treatment of certain abnormal skin conditions; it is also an excellent vehicle for therapeutically active drugs for the treatment of pathological skin conditions.

9 Claims, 2 Drawing Figures

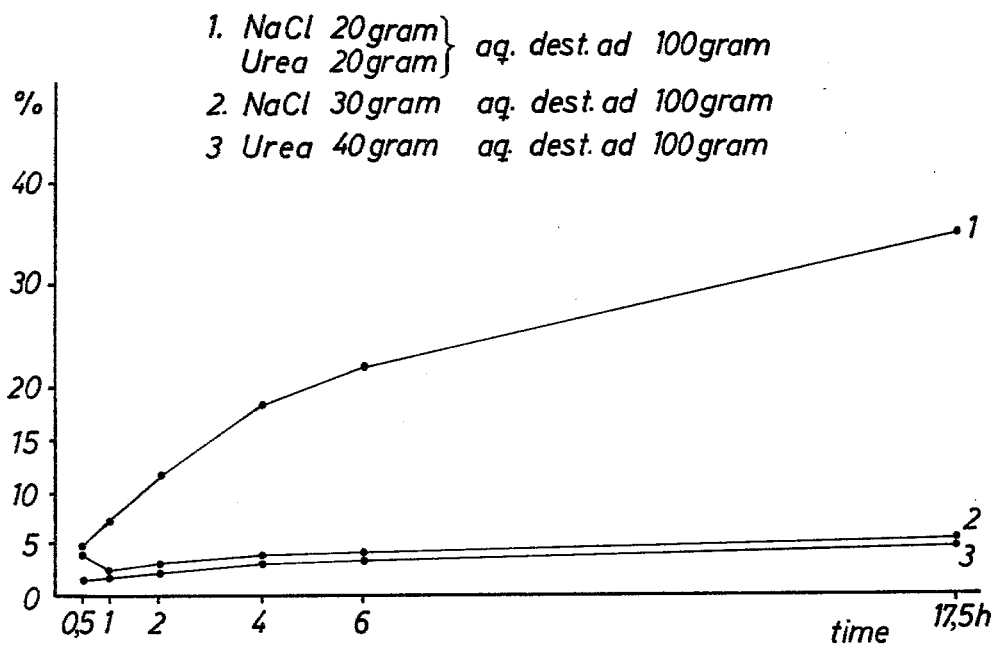
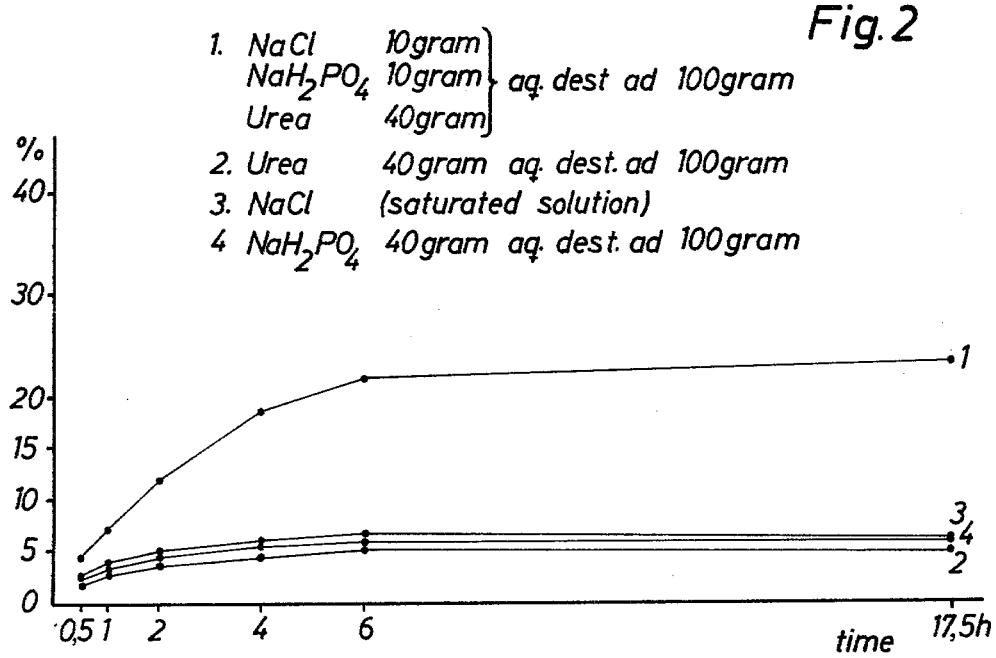

SKIN-TREATING COMPOSITION AND VEHICLE FOR SKIN-TREATING AGENTS

This is a continuation of U.S. Patent Application Ser. No. 712,066, filed Aug. 5, 1976, which is a continuation of U.S. Patent Application Ser. No. 571,746, filed Apr. 25, 1975 now abandoned, which, in turn, is a continuation of U.S. Patent Application Ser. No. 322,197, filed Jan. 9, 1973, now abandoned.

DESCRIPTION OF THE INVENTION

The essential property of the new skin-treating composition is that it exerts a softening action on the corneous layers of the skin and favors the normal release of corneous cells. The corneous layers of the skin on the hands often become dry and rough during the winter which is also true about housewives whose hands some into contact with aqueous detergent solutions. Such changes of the properties of skin may be regarded as slight deviations from the normal and not as skin diseases and the composition according to the invention may be regarded as a cosmetical product when used for the healing of such skin conditions.

However, there are also a number of skin diseases which cause pathological changes of the properties of the corneous layers of the skin. Examples of such diseases are for instance the following: Ichthyosis, psoriasis and atopical eczema. The novel composition according to the invention exerts a beneficial action also on such pathological changes. The composition can be used as such or as a vehicle for special substances which are specifically active against such skin diseases, for instance cortison, hydrocortison and other steroid compounds, e.g. fluocinolon acetonide and triamcinolon acetonide. Other active substances for which the composition can be used as a vehicle comprise antimycotics, antibiotics, tar and tar products as well as sun-screening agents. The softening action of the new skin-treating composition on the corneous layers of skin enables the active substances to penetrate into the skin more rapidly and completely.

Insofar the new skin-treating composition mainly is used for cosmetical purposes it is also suitable as a carrier for common additives to cosmetical preparations such as perfumes, etc.

The research leading to the new skin-treating composition of the invention was based on the fact that the normal corneous layers of skin differ from the thickened and hardened or pathologically changed corneous layers in that the normal corneous layers contain a certain amount of hygroscopic substances, whereas the thickened, hardened or pathologically changed corneous layers of skin contain a considerably lesser amount of hygroscopic substances.

The use of urea as a skin-treating agent with a softening action on the thickened and hardened corneous layers has been suggested previously. Urea has been used in an aqueous solution or in the form of a crean (emulsion of the oil-in-water type) but certain disadvantages were discovered which mainly were due to the fact that urea in an aqueous solution is not stable but decomposed to the formation of carbon dioxide and ammonia. In a urea-containing cream the decomposition of urea leads to phase separation. The urea-containing cream is thus not durable.

The skin-treating composition or vehicle for skin-treating agents according to the invention contains as obligatory compositions urea and a salt in an aqueous solution.

The invention is based on the discovery that the combination or urea and a salt applied to the skin gives a surprising synergistic effect as regards water retention. This synergistic effect is obvious from the enclosed drawing which represents curves obtained by plotting the percentual water uptake by dry pieces of corneous layer from human skin, treated with a composition according to the invention and subsequently dried, in an atmosphere of 76% R.H. and 22° C., against time lapsed.

More specifically, dry pieces of human corneous layer were dipped in test compositions comprising compositions according to the invention and comparative compositions containing the individual components. The excess solution was removed with the aid of filter paper and the pieces of corneous layer were dried in a desiccator (silica gel) to constant weight (about 24 hours). The dried pretreated pieces of corneous layer were then introduced into a climate cabinet kept at 76% R.H. and about 22° C. The test pieces were weighed at intervals of 0.5, 1, 2, 4, 6 and 17.5 hours.

The curves so obtained show that treatment of human corneous layer with solutions containing urea and a salt each per se cause a minor water uptake by the corneous layer of up to about 5% water content after 6 hours, whereas treatment with a solution containing the combination of urea and salt gave a water uptake after 6 hours corresponding to a water content of more than 20% and a final water content of 25–35%.

This increased water content of the corneous layer treated with the composition according to the invention makes the dry pieces of corneous layer pliable and soft which is desirable for successful treating of numerous skin disorders of the above-mentioned kinds.

The ability of the compositions according to the invention to increase the water content of the corneous layer of the skin makes them also suitable as a vehicle for drugs which due to the increased water content in the skin may be kept in a dissolved or semi-dissolved state and can so penetrate the skin layers.

The salt component in the compositions according to the invention can be one or more salts chosen among a number of physiologically compatible salts, i.e. salts which do not exert an unfavorable action on the skin, such as alkali metal salts, especially sodium salts, magnesium salts, ammonium salts, alkyl and alkylol substituted ammonium salts, but also other water soluble salts as e.g. zinc salts give a certain effect. However, best results are obtained with sodium salts especially with NaCl, but good results are also obtained with $Na_2S_2O_3$, $Na_2HPO_4$, $NaH_2PO_4$ and $MgCl_2$. The preferred salt is NaCl.

The aqueous solution of urea and the salt should have a pH within the range 2–8, preferably 3–7. If required, the pH value may be adjusted as is conventional.

The proportion of urea to the salt may be varied within wide limits such as 10:1 to 1:10. However, it is preferred to keep the said range more narrow, such as 5:1 to 1:5. It is especially preferred to keep the ratio urea/salt around 1/1 or somewhat higher.

The concentration of urea and salt in the aqueous phase is not critical. For practical reasons the total concentration is kept rather high, i.e. 10–40% of the aqueous phase, preferably 15–40%, but lower and also higher concentrations such as 50% and above may be used depending on the solubility of the total solute. It is preferred to keep the urea and the salt in total solution even if some undissolved material may be tolerated.

In many cases the new composition is used without a lipid or disperse phase, e.g. in moist bandages. It is also possible to impregnate fabrics with an aqueous solution containing urea and salt and pack the fabrics in sealed packages so that no moisture will evaporate before use.

The new composition can also be used in the form of aerosol sprays, such as foam aerosols.

It is often suitable to use the new composition in the form of ointments, creams, emulsions or dispersions in which case the composition contains greater or lesser amounts of a conventional lipid substance as the disperse phase.

The formation of emulsions or dispersions is well-known in the art. The presence of the salt in the aqueous phase may cause difficulties in emulsion formation due to phase separation. The choice of a correct emulsifier or dispersing agent is, however, within the skill of the average expert. Examples of useful emulsifiers for emulsions containing inorganic salts are the monoglycerides of fatty acids, such as monolauric acid glyceride and monomyristic acid glyceride. A preferred composition according to the invention comprises the aqueous phase in combination with an emulsifier combination of the above-mentioned type as the sole lipid which then acts as a means for giving the aqueous phase a viscous consistence suitable for application to the skin, i.e. as a thickening agent.

The lipid content is usually 5–50% by weight of the total composition including the emulsifiers, preferably 10–40% by weight.

Further optional components in the new skin-treating composition are the following:

(a) Amino acids occurring in the corneous layers of the human skin or derivatives obtained thereof such as glycine, serine, ornithine, citrulline, arginine and especially betaine;

(b) surface-active substances (emulsifiers) which are present when the skin-treating composition contains a disperse lipid phase;

(c) wetting agents which facilitate the spreading and penetration of the composition into the skin.

As has been stated above the skin-treating composition according to the invention may contain a lipid phase but this is not essential. However, when the skin-treating composition according to the invention contains a lipid phase it is preferred that the aqueous phase is the continuous one and the lipid phase the disperse phase, i.e. the composition is preferably an emulsion of the oil-in-water type.

As the lipid component saponifiable and also non-saponifiable lipids may be used as well as natural products containing saponifiable and also unsaponifiable lipids, such as wool fat. Hydrocarbons may also be used, e.g. paraffin oil, petrolatum or other petroleum products commonly used in ointments or creams.

The skin-treating composition according to the invention can further contain additives commonly used in cosmetic compositions.

Clinical tests on dermatological patients with different types of dry skin have verified the benefical effect of the compositions of the invention.

The invention is further elucidated by the following non-limiting examples.

EXAMPLE 1

| Skin-treating solution. | |
|---|---|
| Urea | 20 |
| Sodium chloride | 20 |
| Distilled water | 60 |

EXAMPLE 2

| Skin-treating solution. | |
|---|---|
| Urea | 20 |
| Sodium chloride | 10 |
| Sodium dihydrogen phosphate | 10 |
| Distilled water | 60 |

EXAMPLE 3

| Skin-treating dispersion. | |
|---|---|
| Urea | 10 |
| Sodium chloride | 10 |
| Monolauric acid glyceride | 9 |
| Monomyristic acid glyceride | 21 |
| Distilled water | 50 |

EXAMPLE 4

| Skin-treating solution. | |
|---|---|
| Urea | 10 |
| Sodium chloride | 5 |
| Sodium dihydrogen phosphate | 5 |
| Monolauric acid glyceride | 9 |
| Monomyristic acid glyceride | 21 |
| Distilled water | 50 |

EXAMPLE 5

| Skin-treating dispersion. | |
|---|---|
| Urea | 10 |
| NaCl | 5 |
| $Na_2S_2O_3$ | 5 |
| Monolauric acid glyceride | 9 |
| Monomyristic acid glyceride | 21 |
| Distilled water | 50 |

In the compositions according to Examples 1–5 above other salts may also be used with favorable results, e.g. $MgCl_2$ and $Na_2HPO_4$.

I claim:

1. A composition for softening dry or rough skin which is capable of water retention by the corneous layer of the skin in contact therewith consisting essentially of:
    (a) an aqueous solution of urea and a physiologically compatible salt selected from the group consisting of NaCl, $Na_2S_2O_3$, $Na_2HPO_4$, $NaH_2PO_4$ and $MgCl_2$, said solution having a pH of 2–8, the concentration of said urea and salt being 10–40% by weight of the aqueous solution, the weight ratio of urea to salt being within the range from 5:1 to 1:5, the rest being water and
    (b) a dispersed liquid phase in an amount of from 5 to 50% by weight of the composition, said lipid phase consisting essentially of an emulsifier selected from the group consisting of monolauric acid monoglyceride and monomyristic acid monoglyceride.

2. A composition according to claim 1 wherein the physiologically compatible salt is NaCl.

3. A composition according to claim 1 wherein the physiologically compatible salt is $Na_2S_2O_3$.

4. A composition according to claim 1 wherein the physiologically compatible salt is $NaH_2PO_4$.

5. A composition according to claim 1 for softening dry or rough skin which is capable of water retention by the corneous layer of the skin in contact therewith consisting essentially of:
(a) an aqueous solution of urea and a physiologically compatible salt selected from the group consisting of NaCl, $Na_2S_2O_3$, $Na_2HPO_4$, $NaH_2PO_4$ and $MgCl_2$, said solution having a pH of 2-8, the concentration of said urea and salt being 10-40% by weight of the aqueous solution, the weight ratio of urea to salt being within the range from 5:1 to 1:5, the rest being water.

6. A composition for softening dry or rough skin which is capable of water-uptake by the corneous layer of the skin in contact therewith consisting essentially of an aqueous solution of urea and a physiologically compatible salt selected from the group consisting of NaCl, $Na_2S_2O_3$, $MgCl_2$, $Na_2HPO_4$ and $NaH_2PO_4$, wherein the concentration of said urea and salt is 10-40% by weight of the aqueous solution, said solution having a pH of 2-8, and wherein the weight ratio of urea to salt in said aqueous solution is about 1:1, thus providing maximum water retention by said corneous layer.

7. A composition according to claim 6 wherein the physiologically compatible salt is NaCl.

8. A composition according to claim 6 wherein the physiologically compatible salt is $Na_2S_2O_3$.

9. A composition according to claim 6 wherein the physiologically compatible salt is $NaH_2PO_4$.

* * * * *

UNITED STATES PATENT AND TRADEMARK OFFICE
CERTIFICATE OF CORRECTION

PATENT NO. : 4,234,603
DATED : November 18, 1980
INVENTOR(S) : Gunnar P.E. Swanbeck It is certified that error appears in the above–identified patent and that said Letters Patent are hereby corrected as shown below:

Claim 1 (column 4, line 67) amend "liquid phase" to read -- lipid phase--

Claim 5 (column 5, line 14) delete "(a)"

Signed and Sealed this

Twenty-sixth Day of May 1981

[SEAL]

Attest:

RENE D. TEGTMEYER

Attesting Officer

Acting Commissioner of Patents and Trademarks